US008968228B2

(12) United States Patent
Graddon et al.

(10) Patent No.: US 8,968,228 B2
(45) Date of Patent: Mar. 3, 2015

(54) ANKLE BRACE AND METHOD OF USING SAME

(75) Inventors: Marcia Graddon, Centreville, VA (US); Steven Neufeld, Washington, DC (US)

(73) Assignee: N&G Bracing Innovations, LLC, Washington, DC (US)

( * ) Notice: Subject to any disclaimer, the term of this patent is extended or adjusted under 35 U.S.C. 154(b) by 329 days.

(21) Appl. No.: 12/768,051

(22) Filed: Apr. 27, 2010

(65) Prior Publication Data

US 2011/0021963 A1     Jan. 27, 2011

Related U.S. Application Data

(60) Provisional application No. 61/173,006, filed on Apr. 27, 2009.

(51) Int. Cl.
| | | |
|---|---|---|
| *A61F 5/00* | (2006.01) | |
| *A61F 5/37* | (2006.01) | |
| *A61F 5/01* | (2006.01) | |
| A61F 7/00 | (2006.01) | |
| A61F 7/02 | (2006.01) | |

(52) U.S. Cl.
CPC .............. *A61F 5/0127* (2013.01); *A61F 5/0111* (2013.01); *A61F 2007/0044* (2013.01); *A61F 2007/023* (2013.01)
USPC ................................. 602/27; 602/23; 128/882

(58) Field of Classification Search
USPC ................... 602/27, 28, 23, 12, 5, 36, 62, 29; 128/882, 845, 869, 846; 36/15, 24, 12, 36/23, 103, 91, 89, 88, 92, 30 R, 31, 97, 36/44, 145, 173, 178, 140, 25 R, 42
See application file for complete search history.

(56) References Cited

U.S. PATENT DOCUMENTS

| | | |
|---|---|---|
| 3,171,407 A | 3/1965 | Rogers |
| 4,280,489 A | 7/1981 | Johnson, Jr. |
| 4,316,333 A | 2/1982 | Rothschild |
| 4,597,395 A | 7/1986 | Barlow et al. |
| 4,628,945 A | 12/1986 | Johnson, Jr. |
| 4,813,157 A | 3/1989 | Boisvert et al. |
| 4,834,078 A | 5/1989 | Biedermann |
| 4,841,648 A | 6/1989 | Shaffer et al. |
| 4,844,094 A | 7/1989 | Grim |
| 4,977,891 A | 12/1990 | Grim |
| 5,027,801 A | 7/1991 | Grim |
| 5,050,620 A | 9/1991 | Cooper |
| 5,138,774 A | 8/1992 | Sarkozi |
| 5,199,941 A | 4/1993 | Makinen |
| 5,209,722 A | 5/1993 | Miklaus et al. |
| 5,250,021 A | 10/1993 | Chang |
| 5,400,528 A | 3/1995 | Skinner et al. |
| 5,445,602 A | 8/1995 | Grim et al. |

(Continued)

OTHER PUBLICATIONS

Medical Technology Inc., Bledsoe Brace Systems, Bledsoe SikeKick Ankle Brace, 2004. (www.bledsoebrace.com).

(Continued)

*Primary Examiner* — Victoria J Hicks
(74) *Attorney, Agent, or Firm* — Sughrue Mion, PLLC

(57) ABSTRACT

An ankle brace and a method of bracing an ankle including a footplate with a heel portion; an attachable wedge for tilting the ankle brace to adjust a hindfoot varus or valgus position; and an arch support attachable to a top surface of the footplate.

7 Claims, 20 Drawing Sheets

(56) References Cited

U.S. PATENT DOCUMENTS

| | | | |
|---|---|---|---|
| 5,795,316 A | 8/1998 | Gaylord | |
| 5,799,659 A * | 9/1998 | Stano | 128/882 |
| 5,865,778 A | 2/1999 | Johnson | |
| 5,894,684 A | 4/1999 | Sand et al. | |
| 5,951,504 A | 9/1999 | Iglesias et al. | |
| 5,961,477 A | 10/1999 | Turtzo | |
| 5,966,843 A | 10/1999 | Sand et al. | |
| 6,361,514 B1 | 3/2002 | Brown et al. | |
| 7,018,352 B2 | 3/2006 | Pressman et al. | |
| 7,294,114 B1 | 11/2007 | Clement et al. | |
| 2006/0084899 A1 | 4/2006 | Verkade et al. | |
| 2007/0079532 A1 * | 4/2007 | Ramirez | 36/140 |
| 2009/0076425 A1 | 3/2009 | Schwartz | |
| 2009/0247920 A1 | 10/2009 | Clements et al. | |
| 2009/0247922 A1 | 10/2009 | Clements et al. | |

OTHER PUBLICATIONS

Darco International, Inc., Darco Web (TM) Ankle Suport.
Airlift PTTD Brace, Aircast, DJO Incorporated, printed Apr. 21, 2008 (www.aircast.com/index.asp/fuseaction/products.detail/cat/1/id/93).
Advertisement to Health Professionals, Multi Balance System (TM), Product Information, DARAS Medical Products, Foster City, CA 94404, USA, pp. 1-2. printed Nov. 17, 2006.
Dj Orthopedics, LLC, DonJoy, Velocity Ankle Brace, 2005. dj ortho, Vista, CA 92081. www.djortho.com.

* cited by examiner

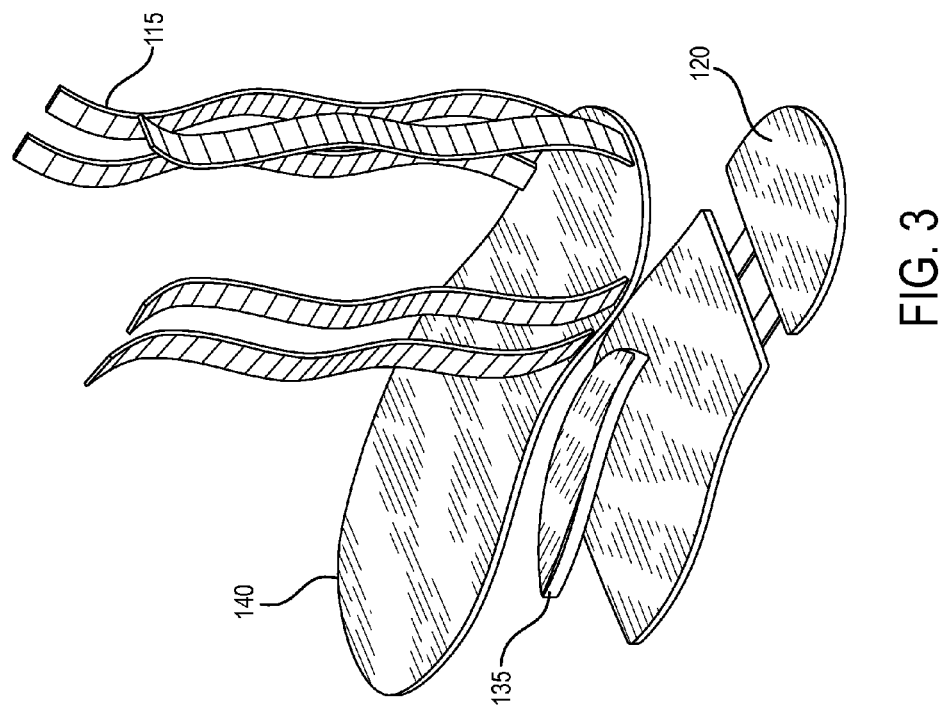
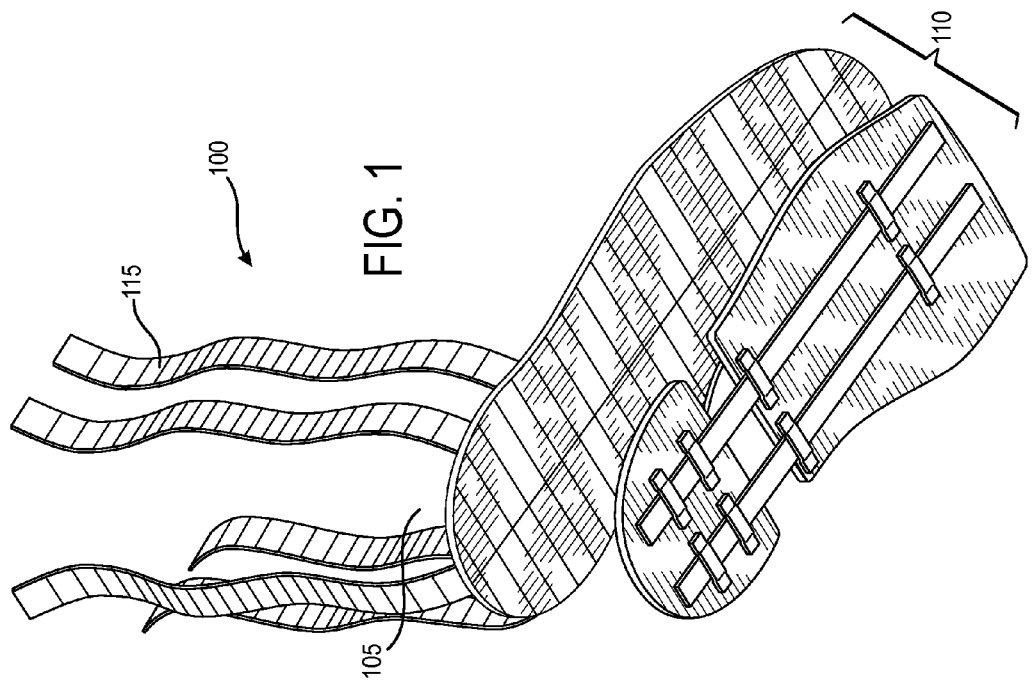

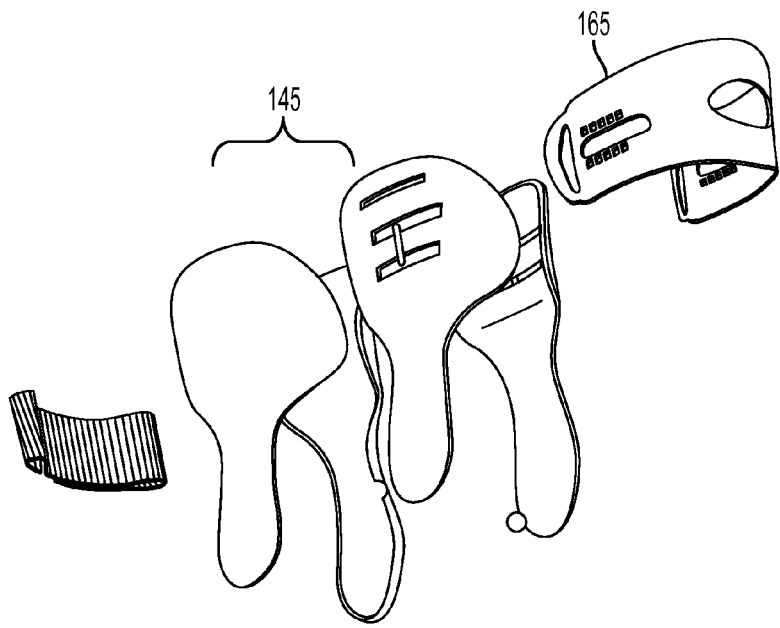
FIG. 9A
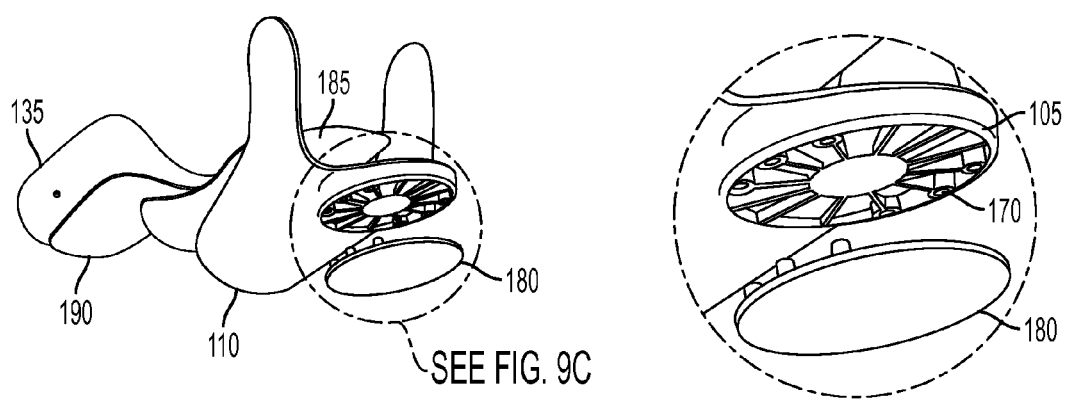
FIG. 9B
FIG. 9C

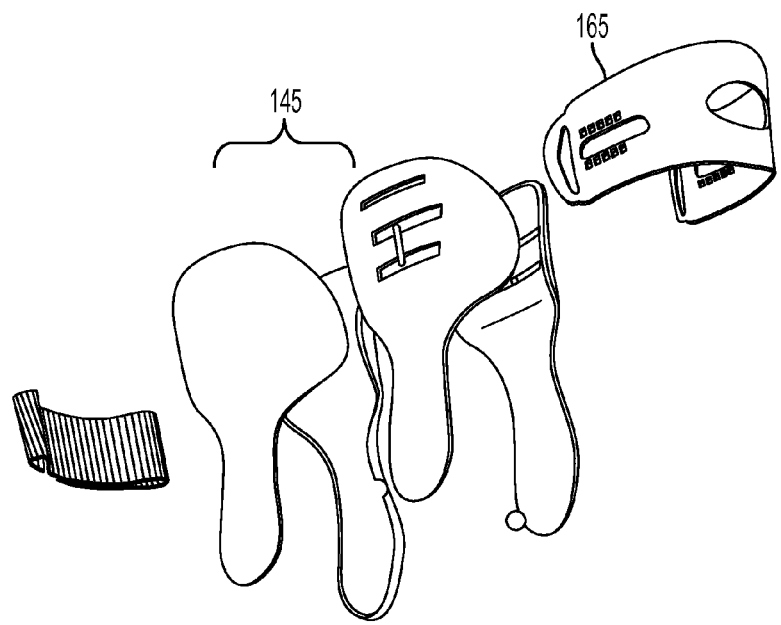
FIG. 12A
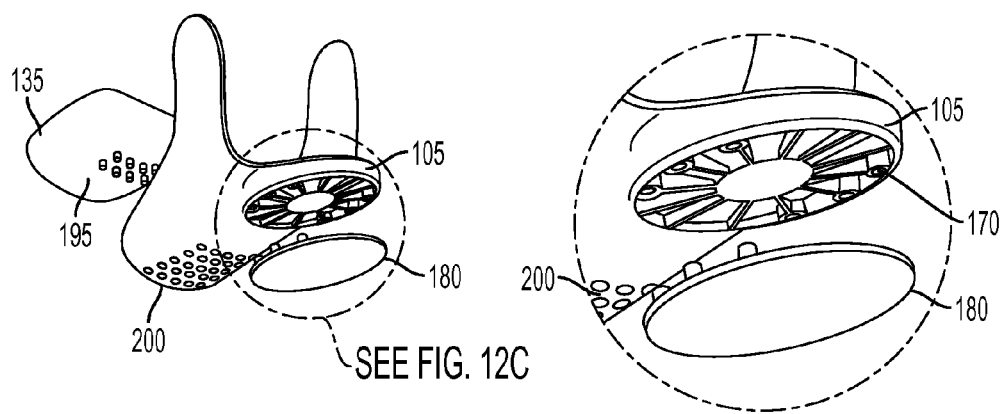
FIG. 12B
FIG. 12C

US 8,968,228 B2

ANKLE BRACE AND METHOD OF USING SAME

FIELD OF THE INVENTION

The present invention relates to an ankle brace and to a method of using the ankle brace to treat an injury and/or to provide support.

BACKGROUND OF THE INVENTION

There are several ankle braces known in the art. However, known ankle braces are not readily customizable and in particular do not provide exact positioning of an arch support according to the length and height of an individual's foot. Another purpose of the ankle brace is to control hindfoot varus and valgus better than known ankle braces.

SUMMARY OF THE INVENTION

One objective of the invention is to provide an ankle brace that allows for the exact positioning of an arch support according to the length and height of an individual's foot.

An advantage of the invention is the ankle brace may be worn inside a shoe, and is easy to put on and take off.

An advantage of the present invention is that the ankle brace provides ankle stability by preventing abnormal ankle inversion and eversion. The ankle brace may allow for ankle range of motion with unrestricted dorsiflexion and plantarflexion. The ankle brace may provide hindfoot valgus and varus correction and stability. The ankle brace may provide stability to anterior translation of the tibia on the talus with the use of a supportive ankle sleeve.

Another advantage of the invention is that the ankle brace allows for compression of the ankle along with heating and cooling of the ankle.

The above object and advantages may be satisfied by an ankle brace that includes a heel portion comprising at least one heel strap, and a foot plate. The foot plate includes (1) a base comprising at least one section moveable along a sliding mechanism which is attached to a bottom surface of the base, thereby allowing adjustment of the ankle brace according to an individual's arch length; (2) an arch pocket attached to a top surface of the base so that differently-size scaphiod pads may be insertable into the arch pocket to adjust the ankle brace according to an individual's arch height; and (3) a top cover.

According to another aspect of the invention, an ankle brace includes a foot plate; a heel portion of the foot plate having means for tilting the ankle brace to adjust a hindfoot varus or valgus position; at least one upright support connected to the foot plate; and an arch pocket or support attachable to a top surface of the foot plate.

According to another aspect of the invention, an ankle brace includes a foot plate including a heel portion and a front foot portion; a wedge attachable to the footplate at the heel portion for tilting the ankle brace to adjust a hindfoot varus or valgus position; and an arch pocket or support attachable to a top surface of the front foot portion of the foot plate.

According to another aspect of the invention, a method of bracing an ankle includes attaching a wedge to a heel portion of a footplate for tilting the ankle brace to adjust a hindfoot varus or valgus position; and attaching an arch support to a top surface of the front foot portion of the foot plate.

As used herein "substantially", "relatively", "generally", "about", and "approximately" are relative modifiers intended to indicate permissible variation from the characteristic so modified. They are not intended to be limited to the absolute value or characteristic which it modifies but rather approaching or approximating such a physical or functional characteristic.

In the detailed description, references to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated. Thus, the invention can include any variety of combinations and/or integrations of the embodiments described herein.

Given the following enabling description of the drawings, the ankle brace and methods should become evident to a person of ordinary skill in the art.

BRIEF DESCRIPTION OF THE DRAWINGS

FIG. 1 is a bottom perspective view of the ankle brace according to an embodiment of the present invention.

FIG. 3 is a perspective view of the ankle brace of FIG. 1.

FIG. 9(a) is an exploded perspective view of elements of the ankle brace of FIGS. 8(a)-(c). FIG. 9(b) is a detailed lower perspective view of a heel portion according to and embodiment of the present invention. FIG. 9(c) is detailed lower perspective view of the heel portion of FIG. 9(b).

FIG. 12(a) is an exploded perspective view of elements of the ankle brace of FIGS. 8(a)-(c) having a different configuration for attaching an arch pocket or support to the foot plate. FIG. 12(b) is a lower perspective view of a heel portion according to an embodiment of the present invention. FIG. 12(c) is a detailed lower perspective view of the heel portion of FIG. 12(b).

DETAILED DESCRIPTION OF THE EXEMPLARY EMBODIMENTS

FIGS. 1-13 illustrate an ankle brace according to exemplary embodiments of the present invention. The ankle brace has a low profile and is both lightweight and comfortable. In addition, the ankle brace may be worn inside a shoe and is easy to put on and take off. The ankle brace may allow for cooling and heating of the foot and ankle. In specific embodiments, the ankle brace is customizable and provides for the exact positioning of an arch support according to the length and height of an individual's foot. Thus, the ankle brace provides customizable medial arch support.

In specific embodiments, the ankle brace provides ankle stability by preventing abnormal ankle inversion and eversion. The ankle brace may also allow for ankle range of motion with unrestricted dorsiflexion and plantarflexion. The ankle brace may provide hindfoot valgus and varus correction and stability and may provide compression to decrease edema in the foot and ankle.

In specific embodiments, the ankle brace may comprise a breathable fabric, thereby allowing heat and moisture to escape through the brace. The ankle brace may comprise a thermoplastic material which may be heat-molded to provide a custom fit. The ankle brace may be sized so that the left and right side are independently adjustable.

According to embodiments of the present invention, the ankle brace may be used for a variety of purposes, for example, to treat injuries or provide support. In specific embodiments, the ankle brace may be used for at least one of the following indications:
Posterior Tibial Tendon Dysfunction;
Ankle, Subtalar, or Midtarsal injury/arthritis;
Painful Flatfoot deformity (pes planus);
Lateral or Medial Ankle Ligament Sprains;
Subtalar Joint Sprain;
Peroneal Tendonitis;
Posterior Tibial Tendonitis;
Some ankle fractures or follow-up treatment for ankle fractures;
Chronic Ankle Instability;
Post-operative rehabilitation;
Post-Cast removal for extra support; and
Provide extra support for sporting activities.

As shown in FIGS. 1-7, an ankle brace 100 according to an embodiment of the present invention comprises (1) a heel portion 105; and (2) a foot plate 110.

Figure 2:
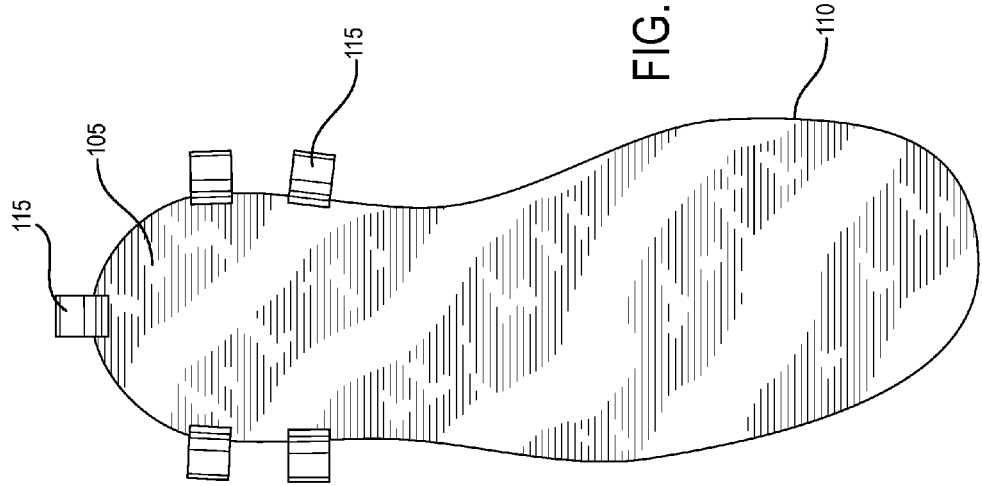
FIG. 2 is a top view of the ankle brace of FIG. 1.

As shown in FIGS. 1-2, the ankle brace 100 comprises a deep and flexible heel portion 105 to cradle the heel in comfort and reduce shock on impact. The heel portion 105 comprises at least one heel strap, for example, three heel straps 115. In embodiments, the heel straps 115 may comprise at least one of a posterior heel strap, a medial heel strap, or a lateral heel strap.

The heel straps 115 may be used to position or wrap an ankle within the heel portion 105 in any suitable manner, for example, through the use of VELCRO®, mechanical fasteners, or an adhesive. According to the present invention, the heel straps 115 can place and hold a heel in a varus or valgus position. The heel straps 115 may be of any effective shape. In embodiments, the heel straps may have a triangular shape with a web design.

In embodiments, the heel portion 105 may have a counter with padded collar (not shown) to prevent heel slippage. The heel portion may comprise an option adjustable heel cap 150 (FIG. 7) that can control varus or valgus position within about a 5 degree range. The adjustable heel cap may be attached be a ratcheting system on an interior medial and lateral hinge.

Figure 4:
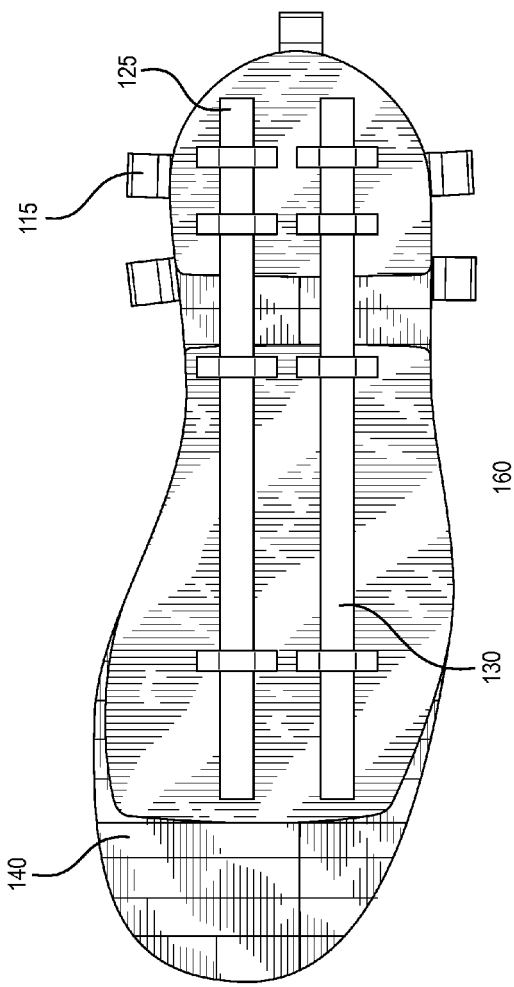
FIG. 4 is a bottom view of the ankle brace of FIG. 1.

Footplate 110 is illustrated in FIGS. 3-4. The foot plate 110 is lightweight. In specific embodiments, the foot plate may comprise a base 120, for example a thermoplastic heat-moldable base, for customization and rigidity. In specific embodiments, the base 120 of foot plate 110 is moveable and adjustable to accommodate different size arch heights and arch lengths as discussed below.

A sliding mechanism 125 may be located on the bottom of the base 120.

The sliding mechanism comprises dual track slide bars 130 to adjust for arch length and arch placement. The base 120 of foot plate 110 may be secured to the sliding mechanism 125 in any suitable manner. For example, base may be secured to the sliding mechanism via a screw tightening closure; a ratchet mechanism; or a snap-fit (baseball hat) mechanism. In embodiments, the base 120 may comprise two separate sections that slide along the sliding mechanism to allow for adjustment of the arch support (arch pocket 135).

According to the present invention, the foot plate 110 comprises an arch pocket 135 on a top side of the base 120. The arch pocket 135 may be attached or connected to the base in any suitable manner, for example, with VELCRO®, a mechanical fastener, adhesive, or via sewing. Different height scaphoid pads (for example, included in a kit) may be selected and placed into the arch pocket 135 to adjust for individual arch heights. The arch pocket 135 may be slid forward or backward along the foot plate via the sliding mechanism 125, which is then fixed to account for arch length.

The foot plate comprises a top cover 140 with a deep heel seat. In embodiments, the top cover 140 may be made of any suitable material, for example a foam such as a cellular urethane foam product (PORON®). The top cover 140 may be attached to the base 120 in any suitable manner, for example, with VELCRO®, mechanical fasteners, or an adhesive.

In embodiments, heel straps 115 come through holes in the top cover or are directly affixed to the top cover to control the hind foot and improve comfort. Advantageously, the top cover may be trimmed down to appropriate foot length.

According to the present invention, the foot plate may also comprise an articulating hinged stirrup design (not shown) to allow for plantarflexion and dorsiflexion, while limiting eversion/inversion/rotation (attached to the stirrups).

Figure 5:
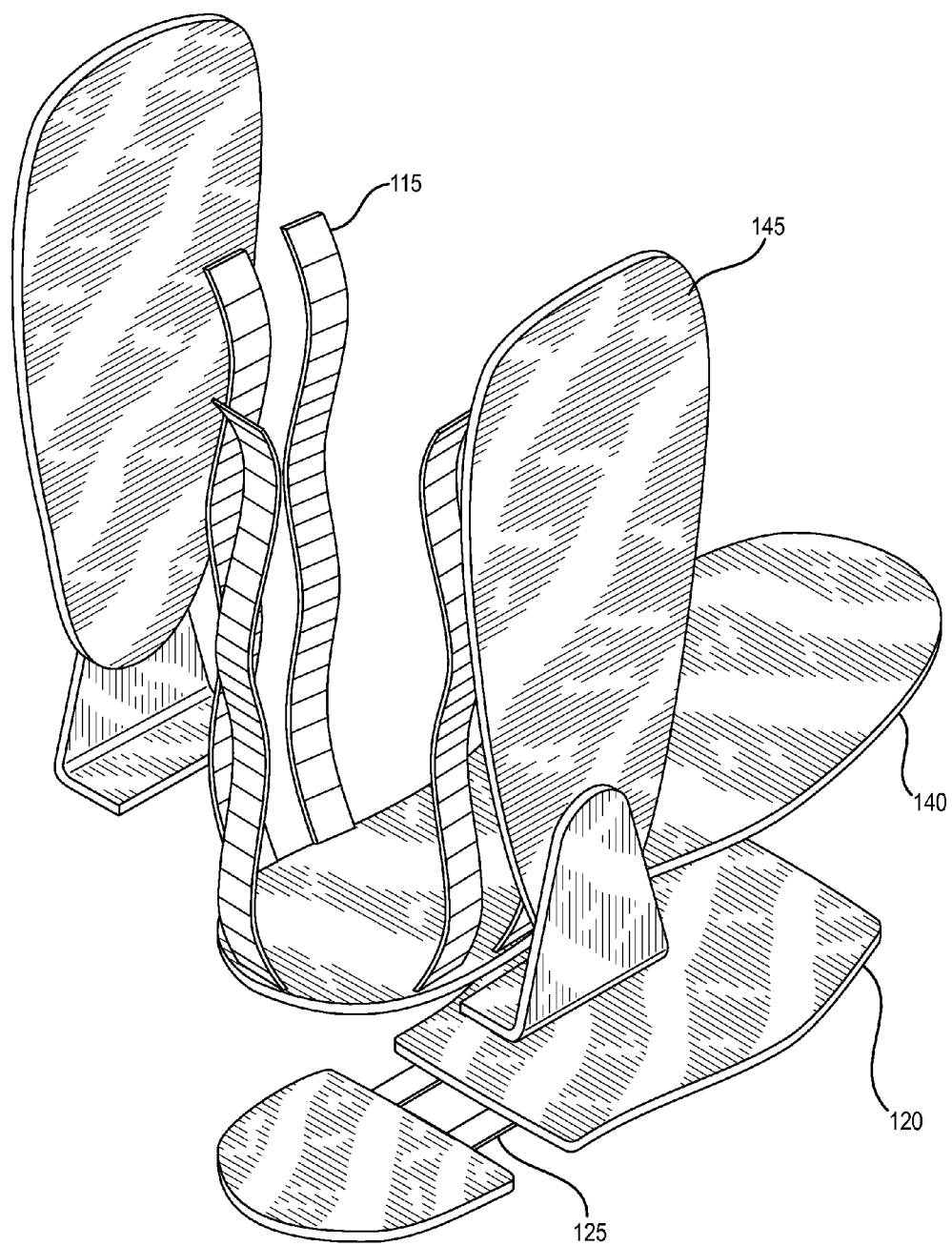
FIG. 5 is a rear perspective view of an ankle brace according to an embodiment of the present invention.
Figure 6:
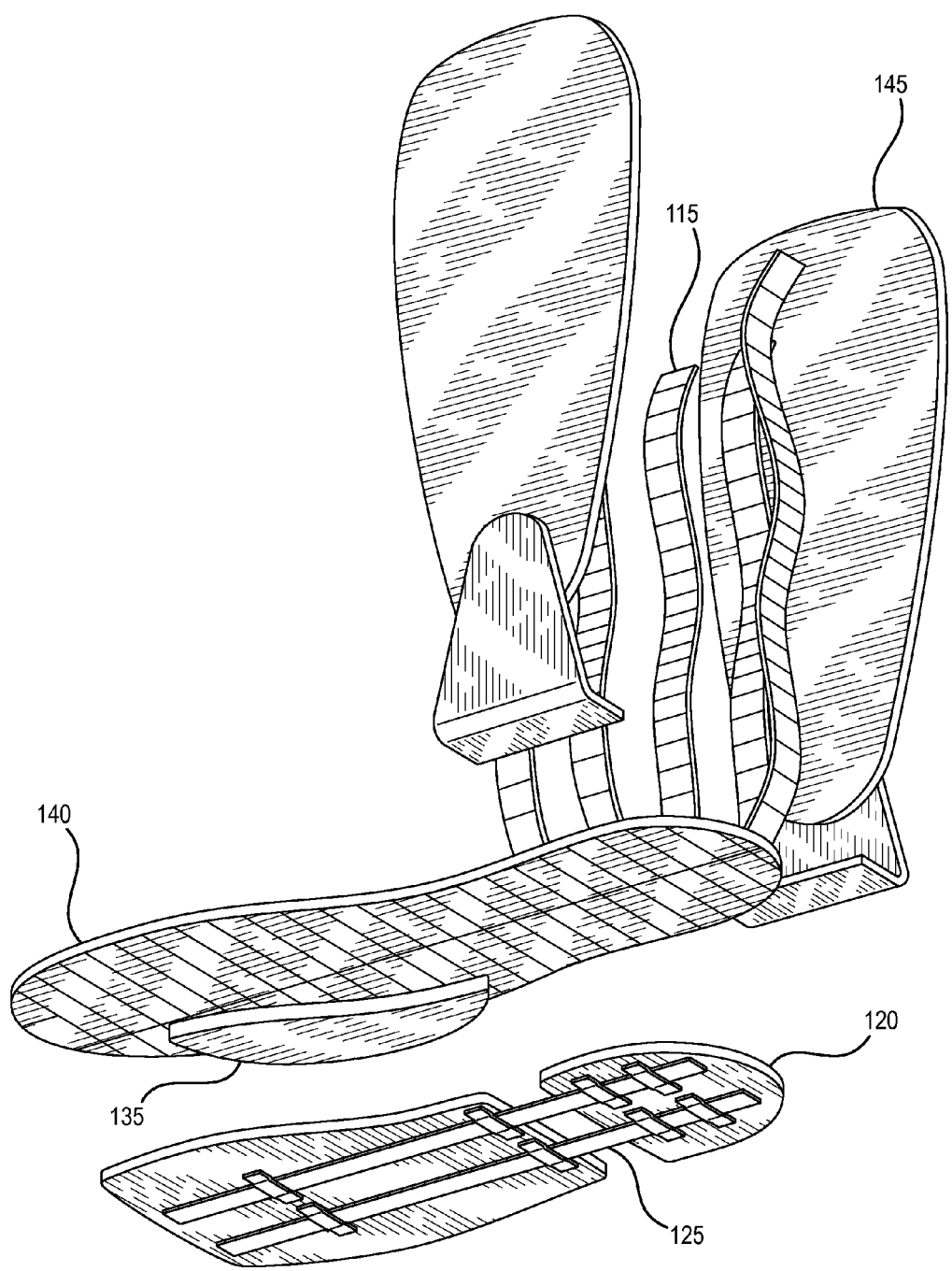
FIG. 6 is a side perspective view of the ankle brace of FIG. 5.

As shown in FIGS. 5-6, the ankle brace 100 may comprise at least one of rigid or semi-rigid lateral or medial upright supports 145 to prevent inversion/eversion. An anterior band closure may be used to provide support and maintain lateral and medial uprights on the tibia crest, thereby preventing anterior subluxation of the ankle.

Figure 7:
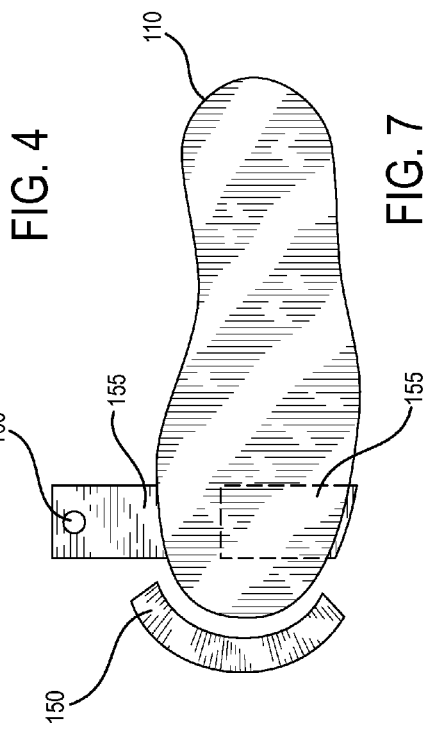
FIG. 7 is a schematic diagram to illustrate a heel cap and ankle sleeve according to an embodiment of the present invention.

In specific embodiments, the ankle brace 100 according to the present invention may comprise an ankle sleeve 155 (FIG. 7). The ankle sleeve may comprise an air cell to allow for at least one of compression, cooling, or warming. The ankle sleeve may comprise NEOPRENE®.

In specific embodiments, the ankle sleeve may comprise a valve 160 which may be attached to an ice, heat, or compression machine (e.g., a VitalWear product). In other embodiments, the ankle sleeve may comprise a bean-bag sleeve with a vacuum seal. Alternatively, the ankle sleeve may comprise a gel-filled at least one removable sleeve (e.g., two sleeves) to allow for short period of cooling and portability or long term use.

Figure 8C:
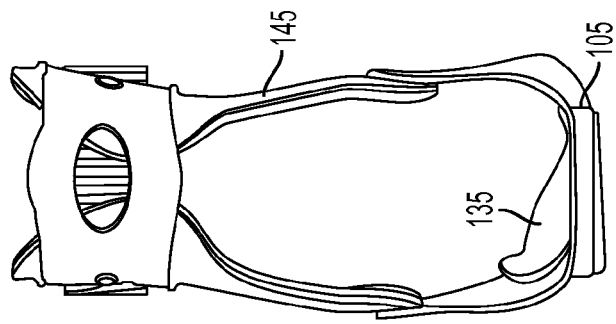
FIGS. 8(a)-(c) are a front view, a side view, and a rear view respectively of an ankle brace according to an exemplary embodiment of the present invention.
Figure 8B:
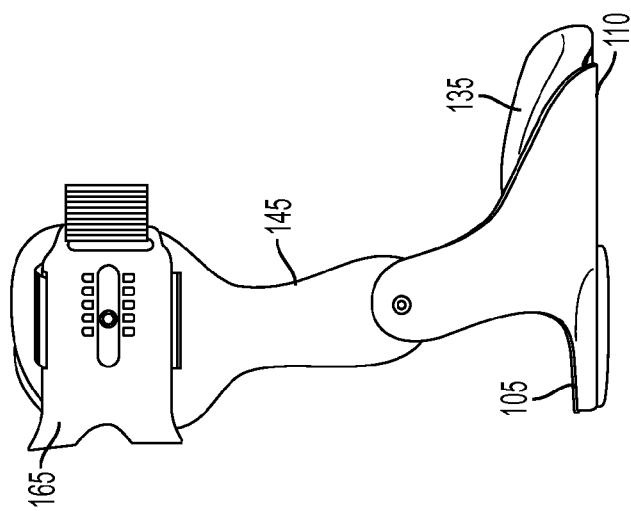
Figure 8A:
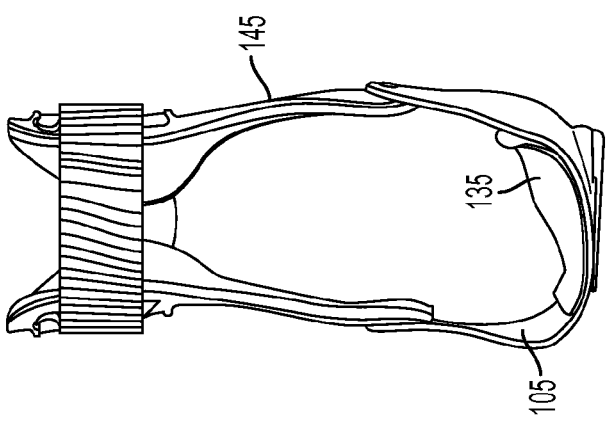

As shown in FIGS. 8(a)-13, the ankle brace 100 according to an exemplary embodiment of the present invention may comprise (1) a heel portion 105; (2) a foot plate 110; (3) an arch pocket 135; and (4) at least one of rigid or semi-rigid lateral or medial upright supports 145 connected to the foot plate, for example, two upright supports, one on each side of the foot plate at or near the heel portion. The lateral or medial upright supports 145 may be integral with or separately attachable to foot plate 110, for example, by a screw or hinge mechanism. The ankle brace may have a collar or cuff 165 at or near the top of the lateral or medial upright supports 145 to adjust the ankle brace to a leg. In specific embodiments, the collar may comprise an adjustable strap. FIGS. 8(*a*)-(*c*) are a front view, a side view, and a rear view of an ankle brace according to the present invention.

Figure 11A:
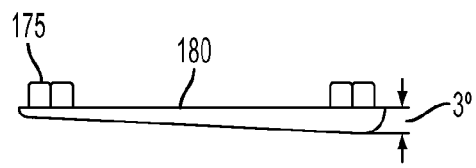
FIGS. 11(a)-(b) are a side view and top view of the disk of the ankle brace of FIGS. 8(a)-(c).
Figure 11B:
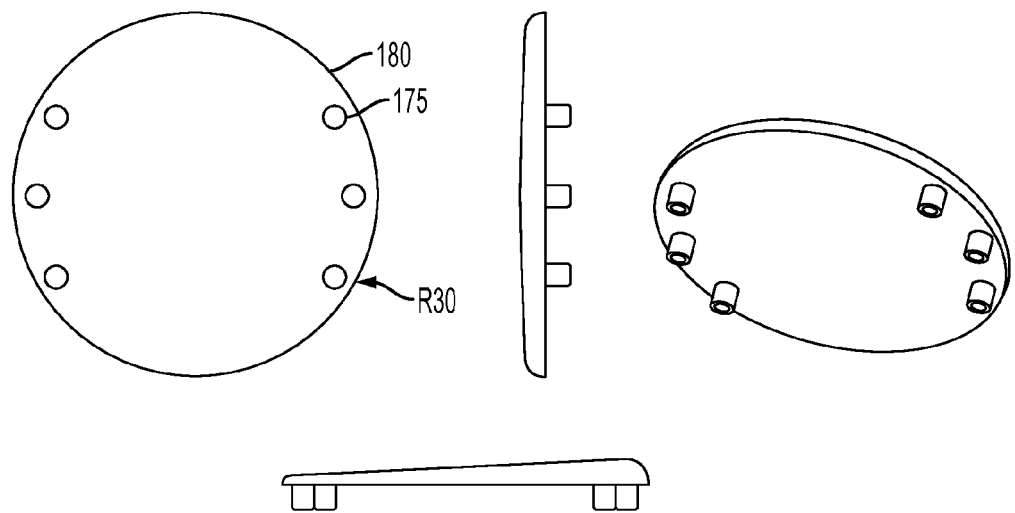
Figure 13:
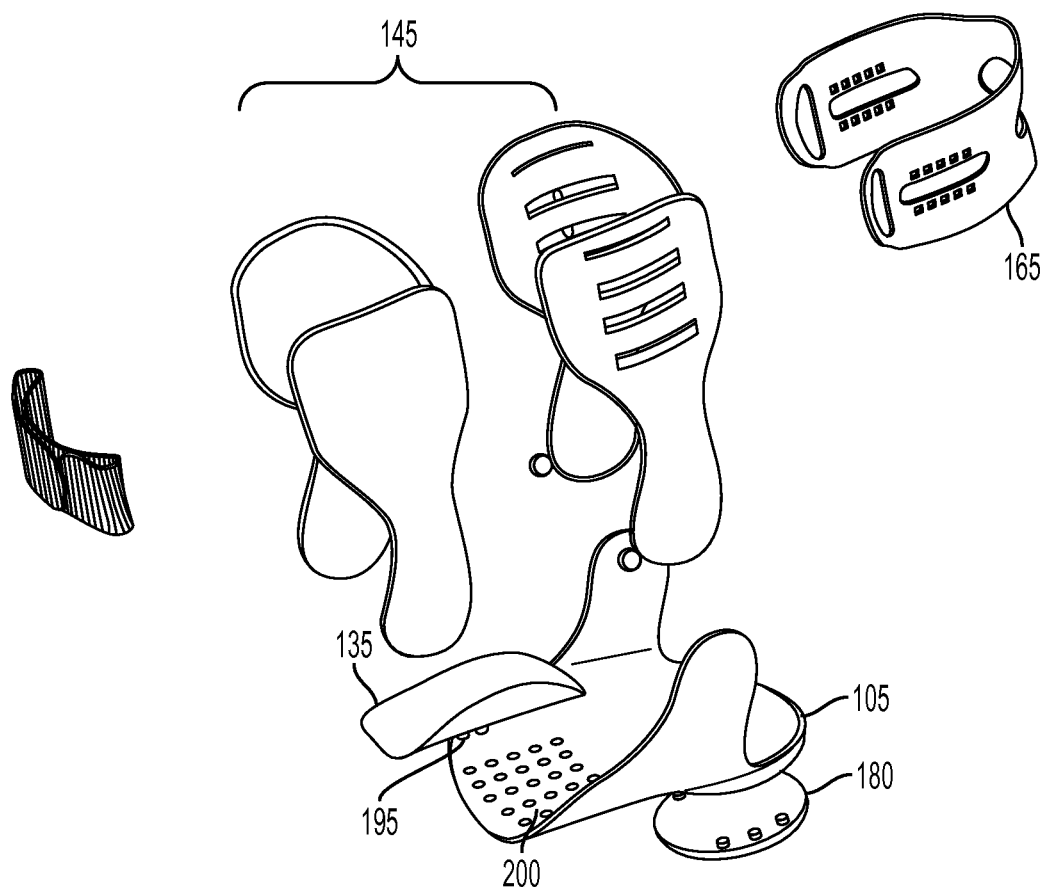
FIG. 13 is an exploded perspective view of elements of the ankle brace of FIGS. 12(a)-(b).
Figures 14A, 14B:
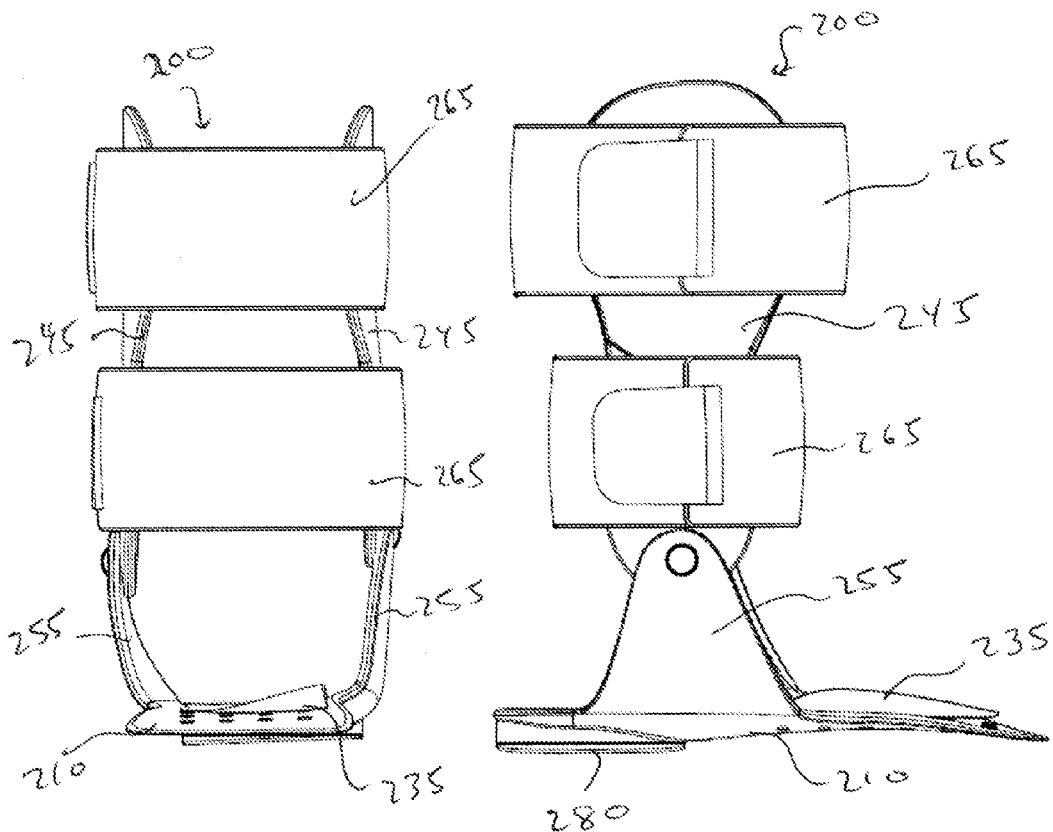
FIGS. 14(a)-(f) are views of another embodiment of the present invention.
Figure 14C:
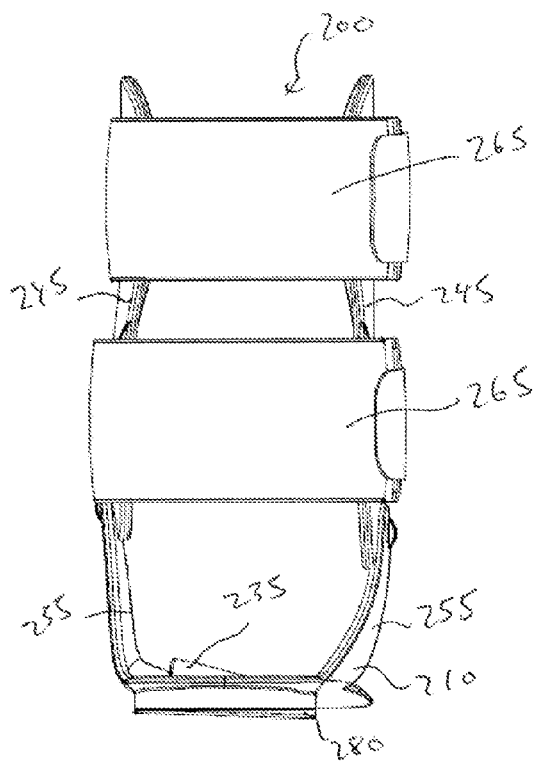
Figure 14D:
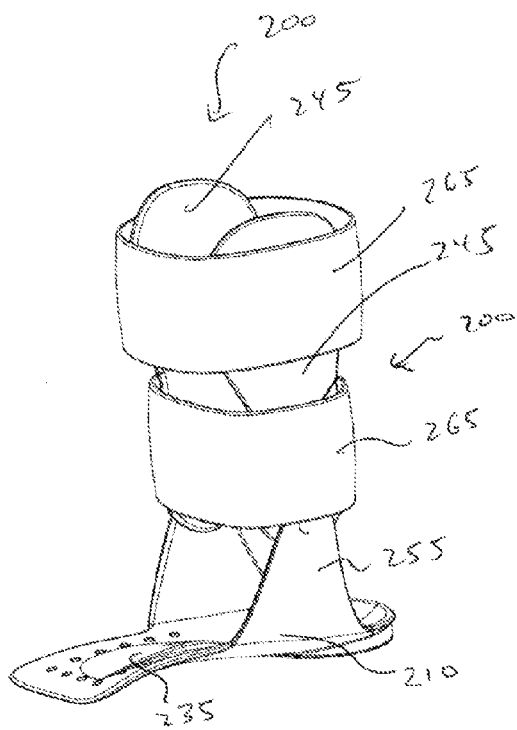
Figure 14E:
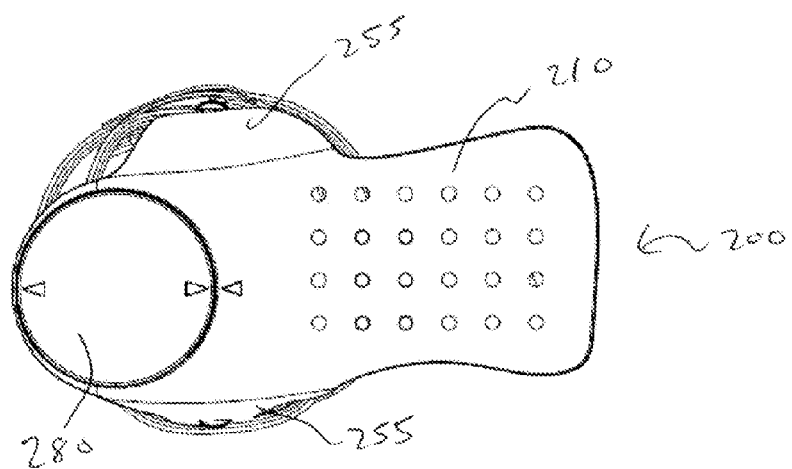
Figure 14F:
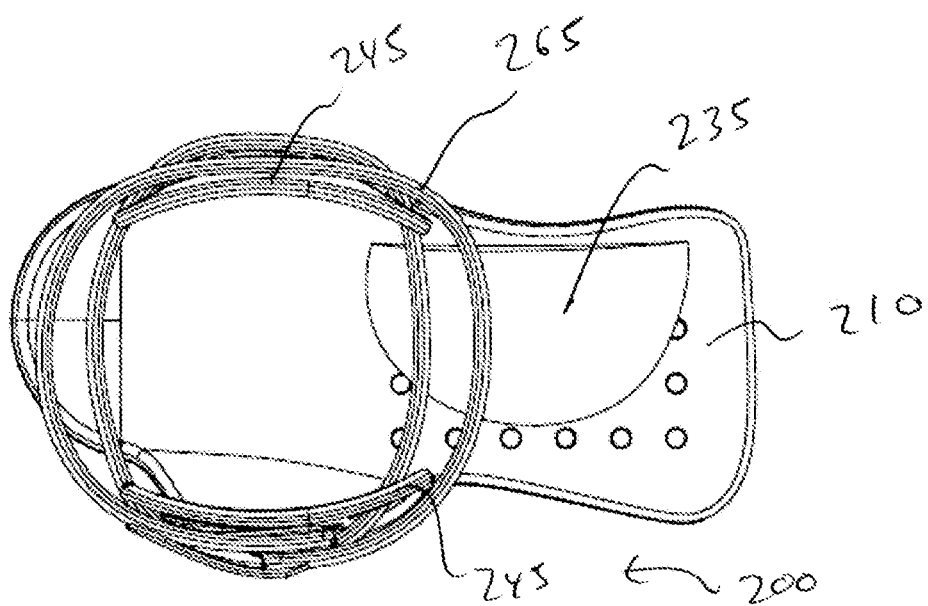

As illustrated in FIG. 9(*a*), in specific embodiments, the lateral or medial upright supports 145 and the collar 165 may comprise one or more separate pieces, for example two pieces to provide stability to the ankle brace. The heel portion 105 of foot plate 110 may have means for tilting the foot plate and ankle brace to adjust a hindfoot varus or valgus position. In specific embodiments, the heel portion 105 may comprise a at least one opening 170 to receive at least one peg 175 located on a top of disk 180, as shown in FIG. 9(*b*) and FIGS. 11(*a*)-(*b*). In specific embodiments, the heel portion may comprise a plurality of openings to receive a corresponding plurality of pegs on the disk. The disk may have a flat top surface and an angled bottom surface, as shown in FIG. 11(*a*) to adjust the heel portion thereby controlling the hindfoot varus or valgus position within about a 5 degree range.

Figure 10:
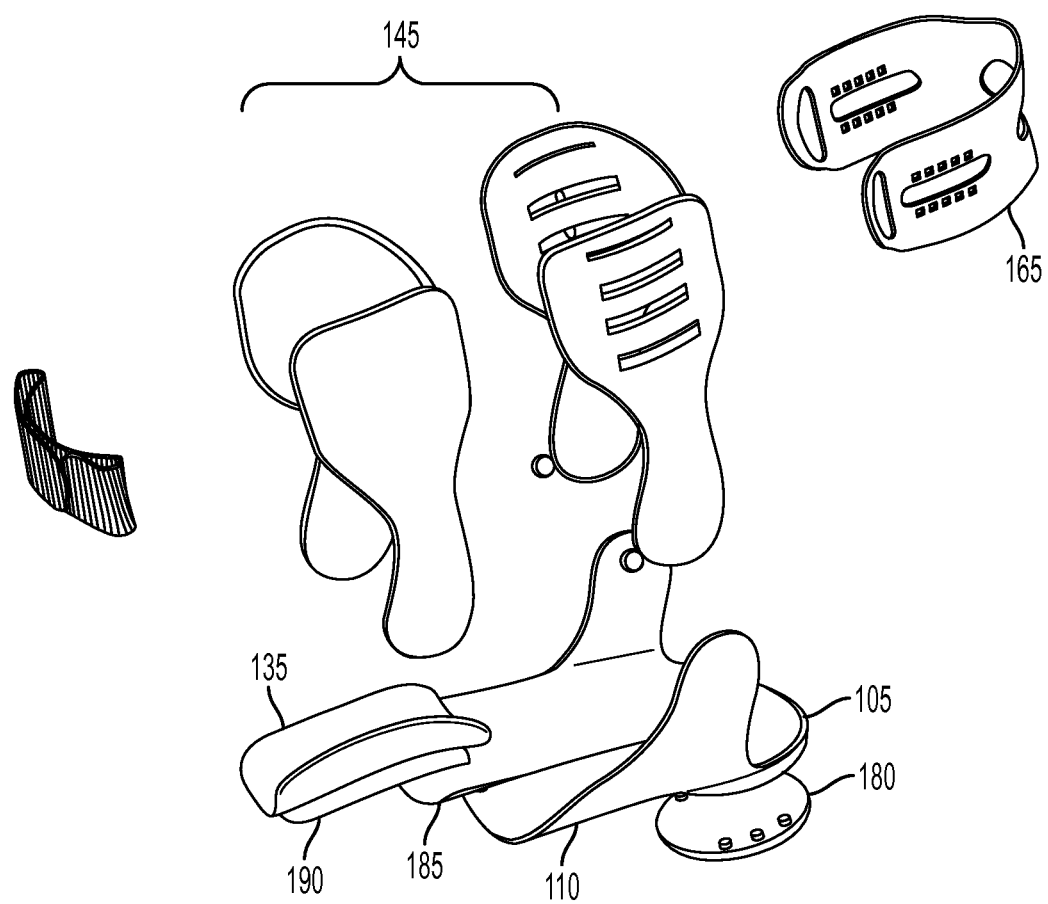
FIG. 10 is an exploded perspective view of elements of the ankle brace of FIGS. 8(a)-(c).

As illustrated in FIG. 10, in specific embodiments, the arch pocket 135 may be attached to the foot plate 10 via a hook and loop configuration, such as VELCRO®. Thus, for example, a loop portion 185 may be attached to a top of the foot plate 110 and a corresponding hook portion 190 may be attached to a bottom of the arch pocket 135 or vice versa. In specific embodiments, an arch support comprising a solid unitary piece may be used rather than an arch pocket.

FIG. 12(*a*)-(*b*) show the elements of the ankle brace of FIGS. 8(*a*)-(*c*), but with a different configuration for attaching the arch pocket or arch support to the foot plate. As illustrated in FIGS. 12(*a*)-(*b*), instead of using a hook-and-loop mechanism to attach arch pocket 135 to foot plate 100, a snap-fit (baseball hat) mechanism is used. As shown in FIGS. 12(*a*)-(*b*) and FIG. 13, the snap-fit configuration may comprise at least one peg, for example a plurality of pegs 195 on a bottom of the arch pocket 135 which are received into at least one corresponding opening, for example a plurality of openings 200, in the foot plate 110, or vice versa.

Figures 15A, 15B:
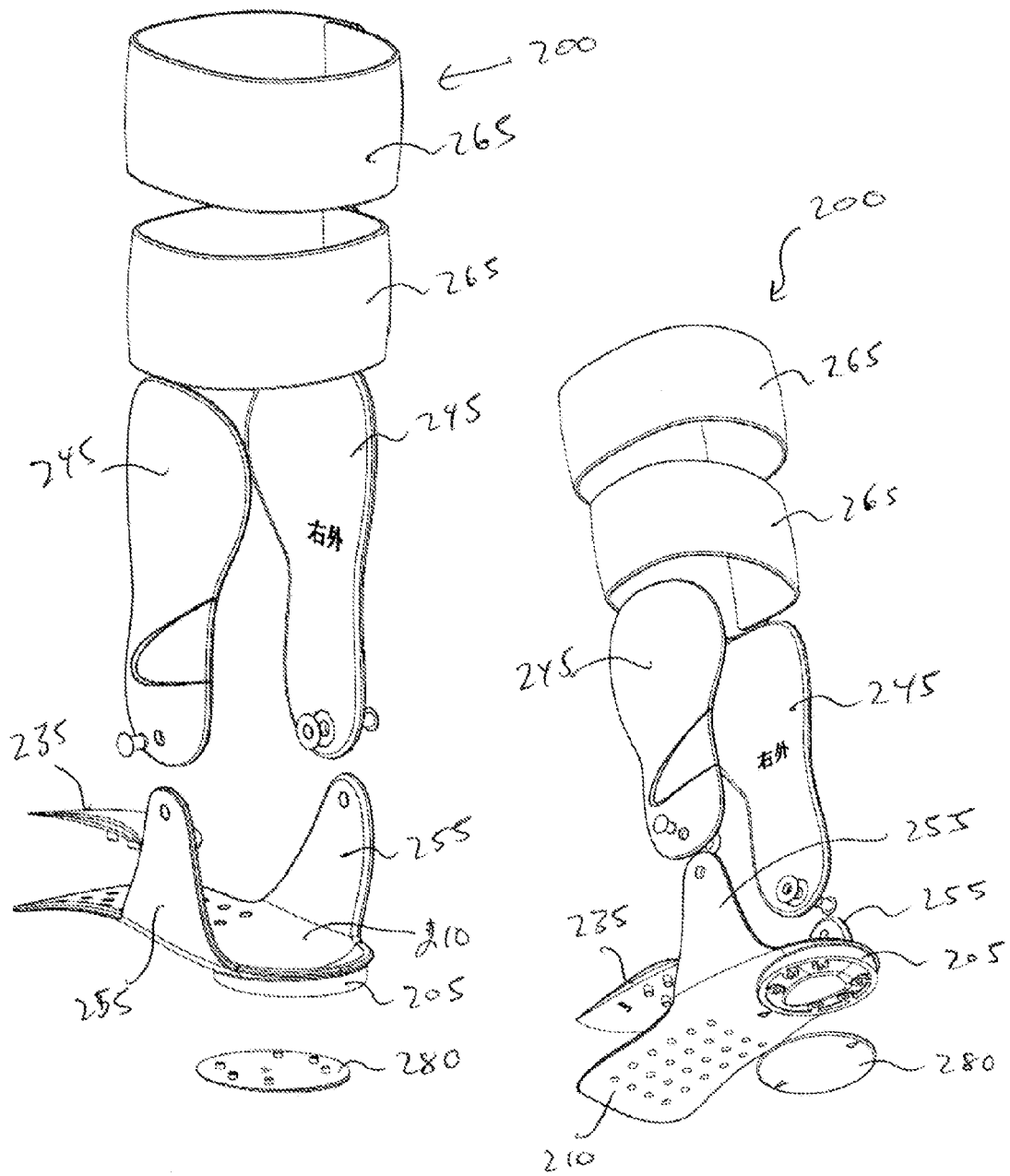
FIGS. 15(a) and 15(b) are top and bottom perspective exploded views of the embodiment shown in FIGS. 14(a)-(f).

As shown in FIGS. 14(*a*)-18(*e*), the ankle brace 200 according to another exemplary embodiment of the present invention may include a foot plate 210, an arch support 235, and a disk 280. FIGS. 14(*a*)-(*f*) are respectively a front view, a side view, a rear view, a perspective view, a bottom view and a top view of the exemplary ankle brace 200. FIGS. 15(*a*) and 15(*b*) are top and bottom exploded views of this embodiment.

Figures 16A, 16B:
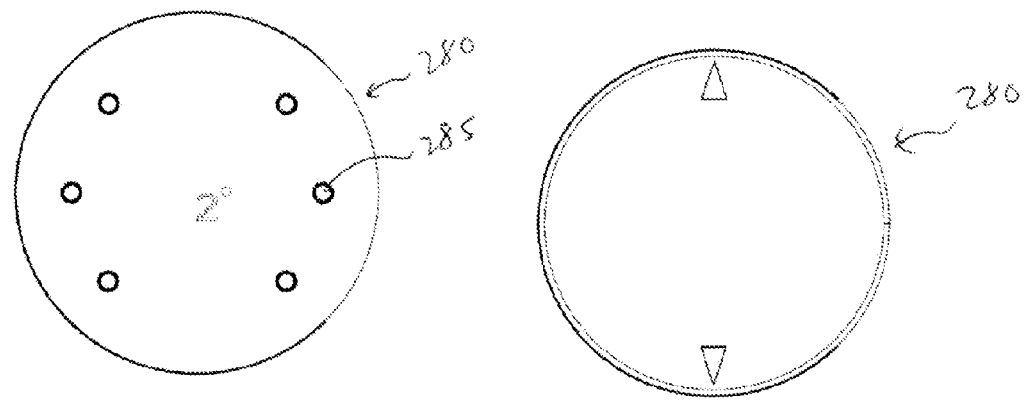
FIGS. 16(a)-(d) are views of a disk of this embodiment.
Figure 16C:
Figure 16D:
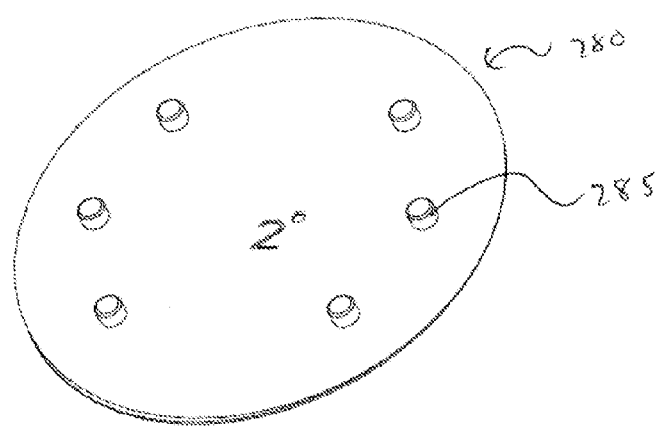

FIGS. 16(*a*)-(*d*) are respectively a top view, bottom view, side view, and perspective view of a disk 280 that is attachable to a heel portion 205 of foot plate 210 to provide tilting of the foot plate 210, and therefore the ankle brace 200, thereby adjusting a hindfoot varus or valgus position. The disk 280 can be a wedge-shaped member and may have a flat top surface and an angled bottom surface to adjust the heel portion thereby controlling the hindfoot varus or valgus position within about a 5 degree range. In this embodiment, the disk 280 is configured to be attached to a bottom surface of the foot plate 210 in either a first direction, in which the varus position of the hindfoot is adjusted, and a second direction, in which the valgus position is adjusted. The second direction is shifted 180 degrees with respect to the first direction. Moreover, the top surface of the disk 280 may include at least one peg 285 (in this embodiment, six pegs 285) that is configured to be received within at least one opening 270 in the foot plate 210.

Figure 17A:
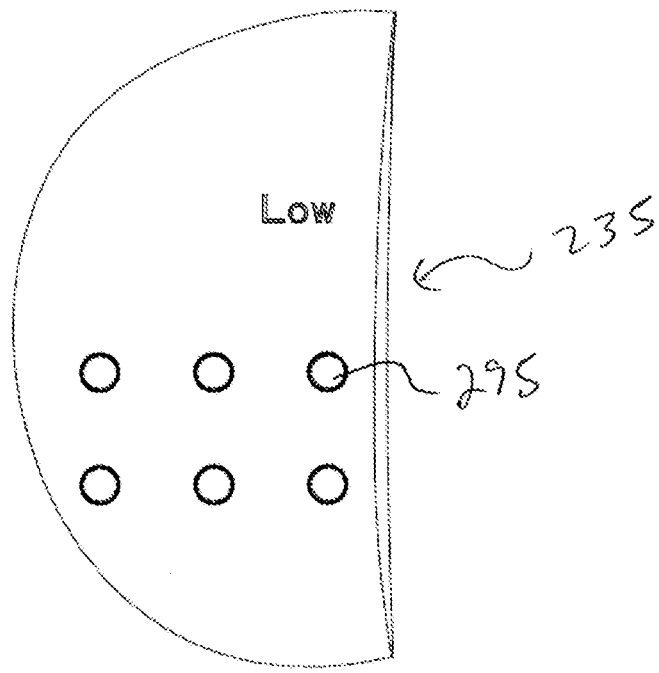
FIGS. 17(a)-(e) are views of an arch support of this embodiment.
Figure 17B:
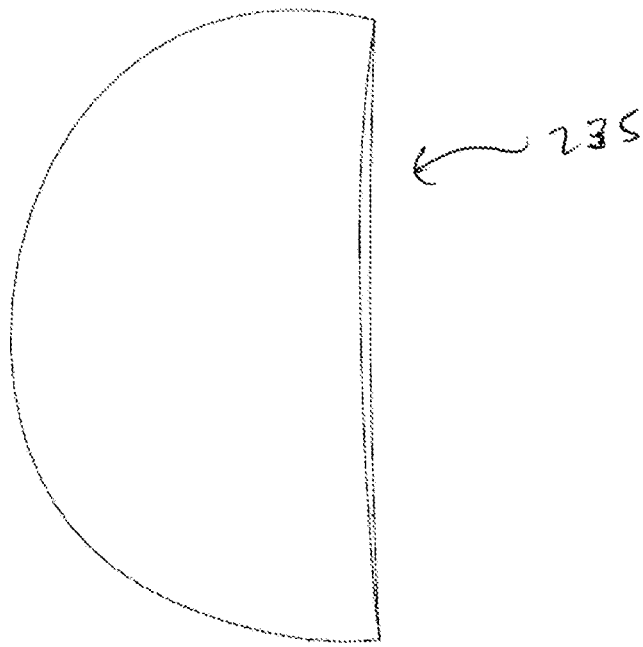
Figure 17C:
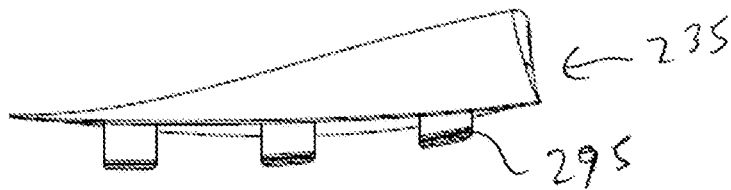
Figure 17D:
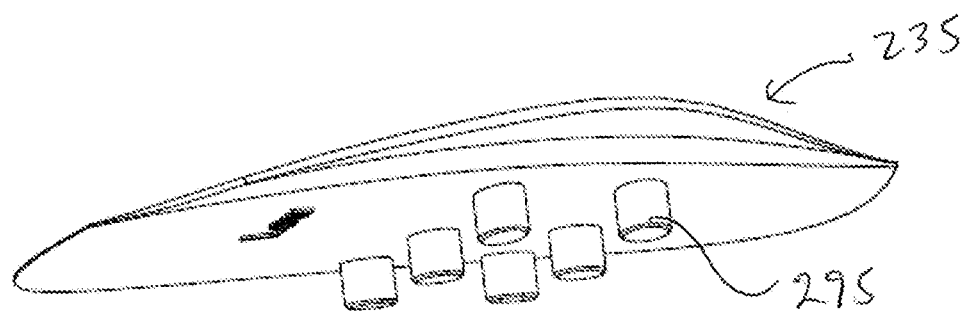
Figure 17:
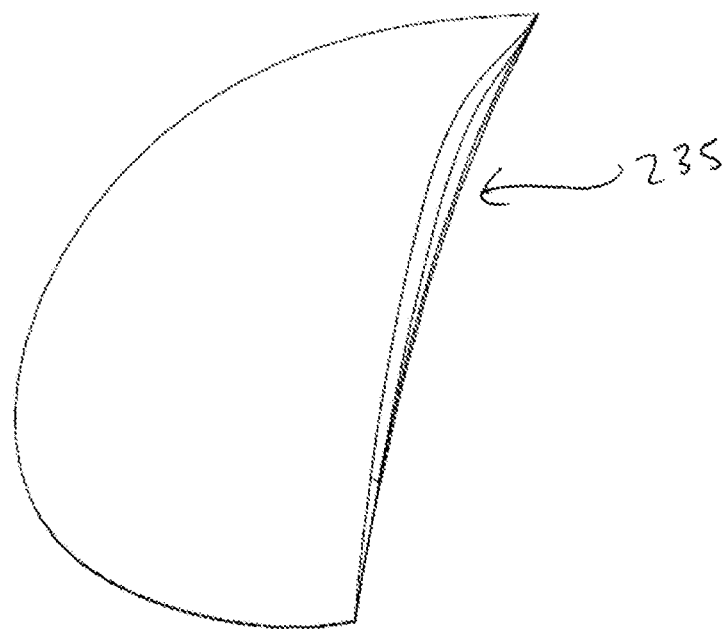
Figure 18A:
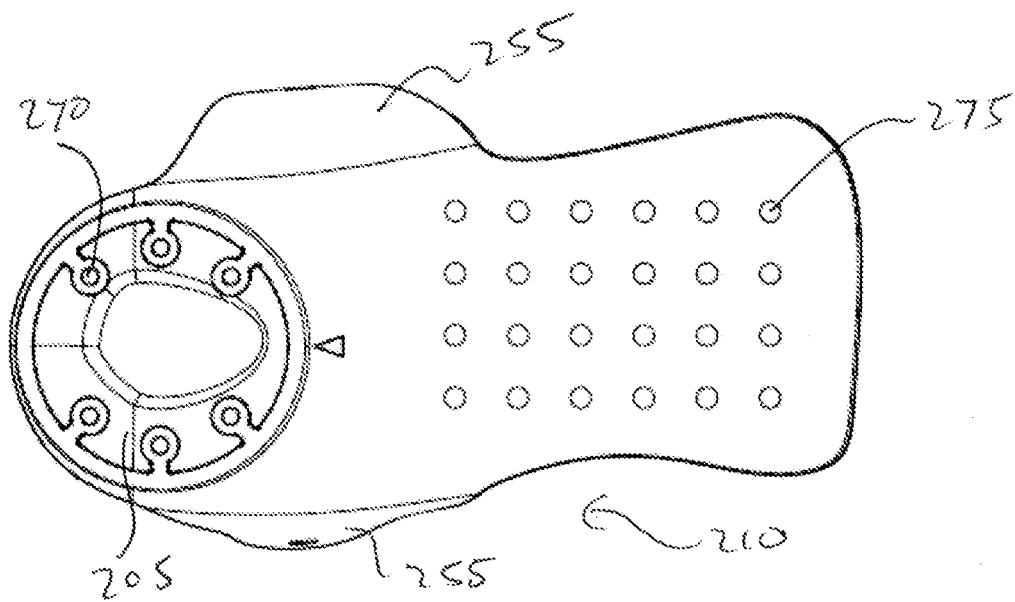
FIGS. 18(a)-(f) are views of a foot plate of this embodiment.
Figure 18B:
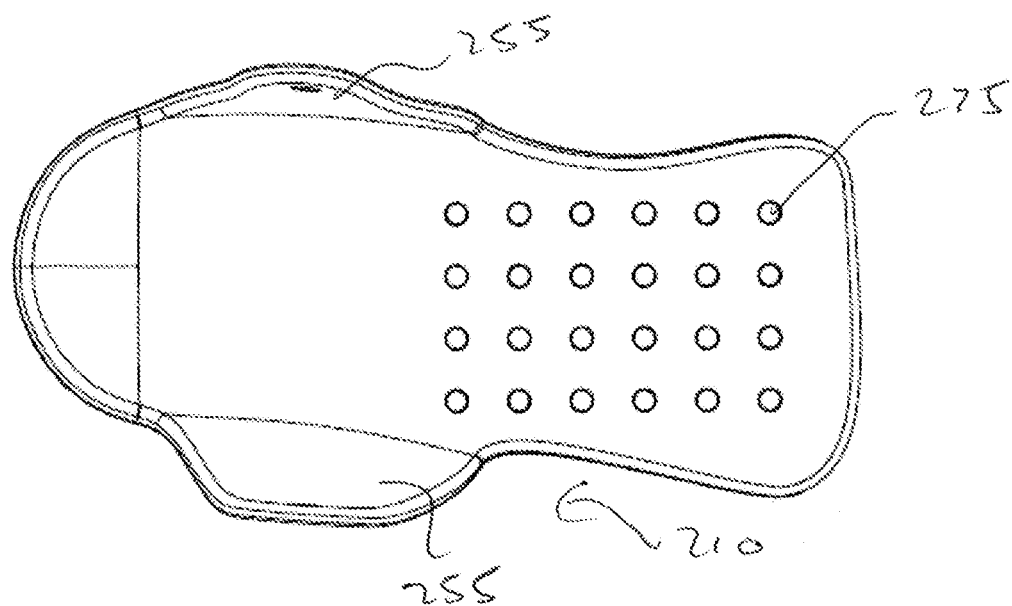
Figure 18C:
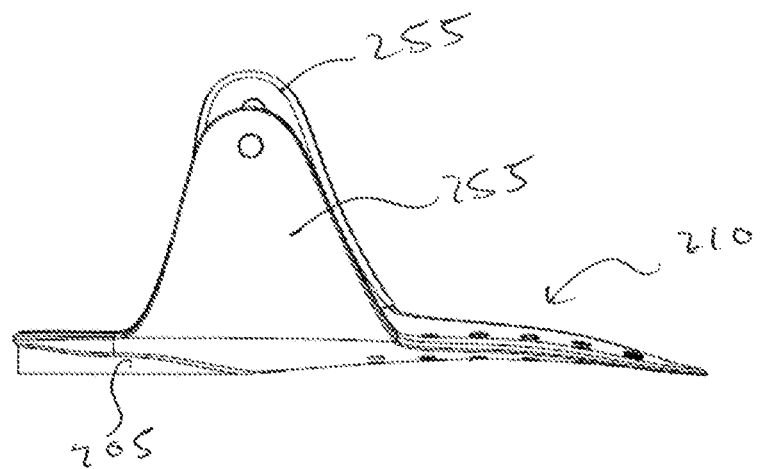
Figure 18D:
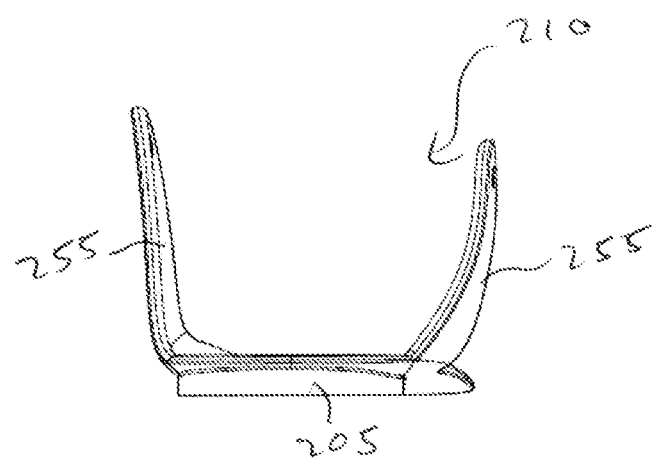
Figure 18E:
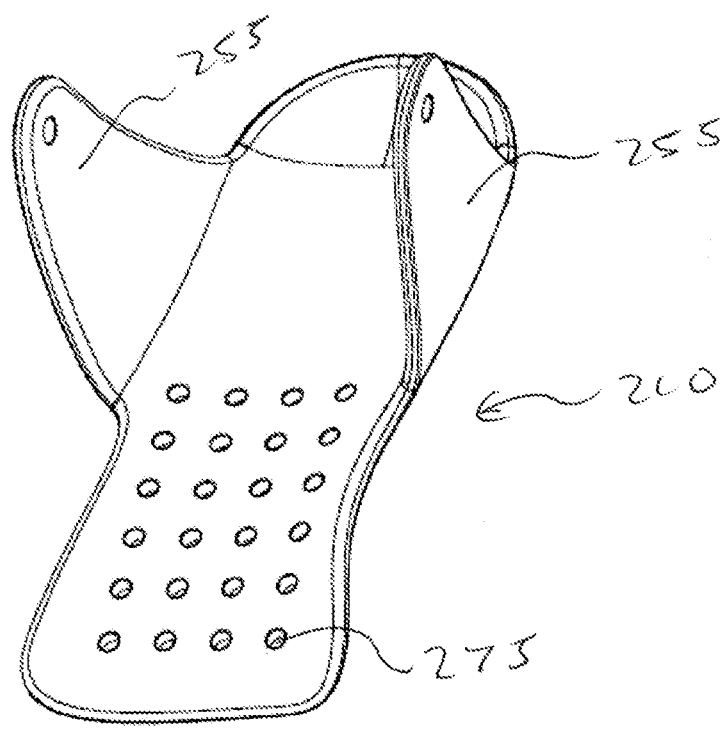
Figure 18F:
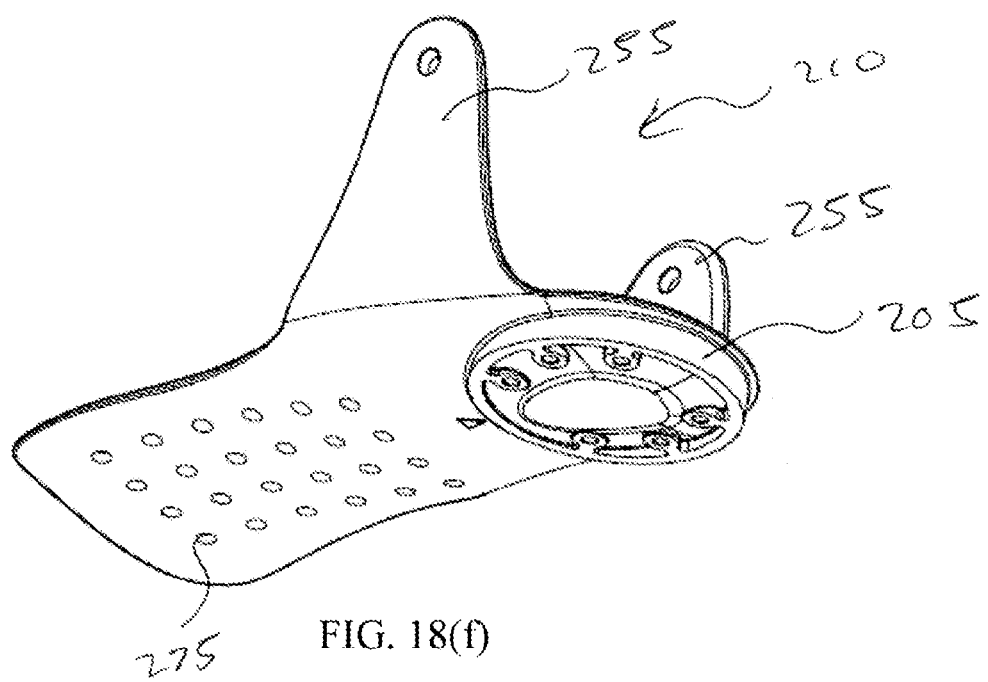

FIGS. 17(*a*)-(*e*) are respectively a bottom view, top view, side view, back view, top perspective view, and bottom perspective view of the arch support 235 of this embodiment. In this embodiment, the arch support has a semi-circular shape. The arch support 235 includes at least one peg 295 provided at a bottom surface of the support 235. The at least one peg 295 is configured to be received within at least one opening 275 in the foot plate 210. By using the removable arch support 235, such as this, the ankle brace 200 can be adjusted for a different size user by changing the size and/or shape of the arch support.

FIGS. 18(*a*)-(*f*) are respectively a bottom view, top view, side view, back view, top perspective view, and bottom perspective view of the foot plate 210 of this embodiment. The foot plate 210 includes rigid or semi-rigid lateral or medial upright supports 245 connected to the foot plate 210. As discussed above, in this embodiment, a front portion of the foot plate 210 includes openings 275 for attachment of the pegs 295 of the arch support 235, and the heel portion 205 of the foot plate includes openings 270 for attachment of the pegs 285 of the disk 280. The foot plate 210 also includes extensions 255 provided on either side of the foot plate 210.

As shown in FIGS. 14(*a*)-(*f*), in this embodiment, two upright supports 245 are provided, one on each side of the foot plate 210 at or near the heel portion 205. In this embodiment, the lateral or medial upright supports 245 are separately attachable to extensions 255 provided on either side of the foot plate 210, for example, by a screw or hinge mechanism. However, the invention is not limited to this configuration and the supports 245 may be integral with the plate 210. The ankle brace 200 may have one or more collars or cuff 265 to adjust the ankle brace 200 to a leg. In this embodiment, the collar 265 includes an adjustable strap.

The ankle brace according to the exemplary embodiments of the present invention may have at least one of the following HCFA billing codes:

L1940 Ankle Foot Orthosis, Plastic Or Other Material, Custom fabricated

L2275—varus/valgus control;

L2270—Addition To Lower Extremity, Varus/valgus Correction ('t') Strap, Padded/lined Or Malleolus Pad;

L2275—Addition To Lower Extremity, Varus/valgus Correction, Plastic Modification, Padded/lined;

L2280—Addition To Lower Extremity, Molded Inner Boot; L2820—Addition To Lower Extremity, Molded Inner Boot;

L1971—Ankle Foot Orthosis, Plastic Or Other Material With Ankle Joint, Prefabricated, Includes Fitting And Adjustment;

L1906—Ankle Foot Orthosis, Multiligamentus Ankle Support, Prefabricated, Includes Fitting And Adjustment;

L3030—foot, Insert, Removable, Formed To Patient Foot, Each; E0217-Water Circulating Heat Pad With Pump;

E0218—Water Circulating Cold Pad With Pump.

The exemplary and alternative embodiments described above may be combined in a variety of ways with each other. Furthermore, the steps and number of the various steps illustrated in the figures may be adjusted from that shown.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

What is claimed is:

1. An ankle brace, comprising:
   a foot plate including a heel portion and a front foot portion;
   a disk-shaped wedge attachable to the foot plate at the heel portion for tilting the ankle brace to adjust a hindfoot varus or valgus position; and an arch support attachable to a top surface of the front foot portion of the foot plate, wherein the foot plate includes a first hole provided at a medial side and a second hole provided at a lateral side of the foot plate, wherein the disk-shaped wedge comprises a first peg on a first side of the disk-shaped wedge and a second peg positioned on a second side of the disk-shaped wedge, the second side being opposite from the first side on the disk-shaped wedge, wherein the first peg and the second peg are capable of being inserted into at least one of the first hole and the second hole, wherein the disk-shaped wedge is configured to be attachable to a bottom surface of the foot plate in a first direction in which the varus position of the hindfoot is adjusted and a second direction in which the valgus position is adjusted, wherein in the first direction, the first peg is inserted into the first hole, and in the second direction, the first peg is inserted into the second hole, wherein the ankle brace is configured to provide -hindfoot valgus and varus correction, wherein in the second direction the wedge is positioned such that it is rotated 180 degrees relative to its position in the first direction.

2. The ankle brace according to claim 1, wherein the wedge comprises a flat top surface and an angled bottom surface.

3. The ankle brace according to claim 1, wherein foot plate includes a plurality of holes in the front foot portion of the foot plate, the arch support comprises at least one peg, and the arch support is attachable to the holes in the front foot portion via the at least one peg of the arch support.

4. The ankle brace according to claim 1, further comprising at least one upright support connected to the foot plate.

5. A method of bracing an ankle, comprising:

attaching a wedge to a heel portion of a foot plate for tilting the ankle brace to adjust a hindfoot varus or valgus position; and attaching an arch support to a top surface of the front foot portion of the foot plate, wherein the foot plate includes a first hole provided at a medial side and a second hole provided at a lateral side of the foot plate, wherein the disk-shaped wedge comprises a first peg on a first side of the disk-shaped wedge and a second peg positioned on a second side of the disk-shaped wedge, the second side being opposite from the first side on the disk-shaped wedge, wherein the first peg and the second peg are capable of being inserted into at least one of the first hole and the second hole, wherein the disk-shaped wedge is configured to be attachable to a bottom surface of the foot plate in a first direction in which the varus position of the hindfoot is adjusted and a second direction in which the valgus position is adjusted, wherein in the first direction, the first peg is inserted into the first hole, and in the second direction, the first peg is inserted into the second hole, wherein the ankle brace is configured to provide hindfoot valgus and varus correction, wherein in the second direction the wedge is positioned such that it is rotated 180 degrees relative to its position in the first direction.

6. The method according to claim 5, wherein the wedge comprises a flat top surface and an angled bottom surface.

7. The method according to claim 5, wherein foot plate includes a plurality of holes in the front foot portion of the foot plate, the arch support comprises at least one peg, and the arch support is attachable to the holes in the front foot portion via the at least one peg of the arch support.

* * * * *